United States Patent
Moritz et al.

(10) Patent No.: US 7,220,590 B2
(45) Date of Patent: May 22, 2007

(54) CONDUCTIVE PLASTIC RACK FOR PIPETTE TIPS

(75) Inventors: Jeffrey R. Moritz, Diamond Bar, CA (US); Allan Avnet, Fountain Valley, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 800 days.

(21) Appl. No.: 10/071,726

(22) Filed: Feb. 8, 2002

(65) Prior Publication Data
US 2003/0152494 A1   Aug. 14, 2003

Related U.S. Application Data

(60) Provisional application No. 60/275,761, filed on Mar. 14, 2001.

(51) Int. Cl.
*G01N 35/10* (2006.01)
*B01L 3/02* (2006.01)

(52) U.S. Cl. .......... 436/49; 422/102; 422/100; 422/104

(58) Field of Classification Search .......... 422/99, 422/100, 102, 104; 436/49
See application file for complete search history.

(56) References Cited

U.S. PATENT DOCUMENTS

| | | | | |
|---|---|---|---|---|
| 3,802,844 A | * | 4/1974 | Sendra et al. | 422/104 |
| 3,819,042 A | * | 6/1974 | Smernoff | 206/443 |
| 3,897,216 A | * | 7/1975 | Jones | 422/104 |
| 3,937,322 A | * | 2/1976 | Cohen | 206/216 |
| 4,060,457 A | * | 11/1977 | Iizuka et al. | 435/283.1 |
| 4,130,978 A | * | 12/1978 | Cohen | 53/444 |
| 4,588,095 A | * | 5/1986 | Mehra | 211/74 |
| 4,605,988 A | * | 8/1986 | Nienhuis et al. | 361/829 |
| 4,676,377 A | * | 6/1987 | Rainin et al. | 206/508 |
| 4,985,207 A | * | 1/1991 | Hayashi | 422/102 |
| 5,190,727 A | | 3/1993 | Hirsch | |

(Continued)

FOREIGN PATENT DOCUMENTS

EP   0849584 A2   6/1998

OTHER PUBLICATIONS http://www.ampacet.com/newsletter/E_blaster/EB_CarbonBlack.htm; Bulletin "What are Conductive Carbon Blacks".*

(Continued)

*Primary Examiner*—Brian R. Gordon
(74) *Attorney, Agent, or Firm*—Maginot, Moore & Beck

(57) ABSTRACT

A conductive plastic tip rack for pipette tips includes a conductive outer shell formed around a support insert. The support insert serves as the skeleton for the tip rack, providing structural support to make the tip rack strong and sturdy. The conductive outer shell includes sidewalls depending from the sides of a face having a plurality of tip seats for receiving a plurality of pipette tips. The conductive outer shell is formed of an electrically conductive plastic. The conductive plastic rack is capable of sufficiently conducting or dissipating electricity such that static electricity existing on a pipette tip placed within the tip rack will flow out of the pipette tip and through the tip rack. By removing the static electricity from the pipette tips placed in the tip rack, static electricity is prevented from disturbing the tips seated in the tip rack.

7 Claims, 2 Drawing Sheets

U.S. PATENT DOCUMENTS

| | | | | |
|---|---|---|---|---|
| 5,248,033 | A | * | 9/1993 | Kos et al. .................... 206/711 |
| 5,318,753 | A | * | 6/1994 | Honda ........................ 422/104 |
| 5,366,088 | A | * | 11/1994 | Hill et al. .................... 206/499 |
| 5,366,896 | A | * | 11/1994 | Margrey et al. .............. 436/48 |
| 5,392,914 | A | * | 2/1995 | Lemieux et al. ............ 206/499 |
| 5,425,506 | A | | 6/1995 | Carey |
| 5,441,702 | A | * | 8/1995 | Lemieux et al. ............ 422/100 |
| 5,605,236 | A | * | 2/1997 | Welch ........................ 211/41.8 |
| 5,609,826 | A | * | 3/1997 | Cargill et al. ................. 422/99 |
| 5,612,000 | A | * | 3/1997 | Lemieux ..................... 422/100 |
| 5,632,388 | A | * | 5/1997 | Morrison et al. ............. 211/74 |
| 5,639,425 | A | * | 6/1997 | Komiyama et al. ........... 422/63 |
| 5,642,816 | A | * | 7/1997 | Kelly et al. ................. 211/60.1 |
| 5,772,962 | A | * | 6/1998 | Uchida et al. ................ 422/67 |
| 5,882,603 | A | * | 3/1999 | Taggart ...................... 422/104 |
| 5,906,795 | A | * | 5/1999 | Nakashima et al. ........ 422/100 |
| 5,948,362 | A | * | 9/1999 | Steinbrenner et al. ...... 422/100 |
| 6,007,779 | A | * | 12/1999 | Lemieux et al. ............ 422/100 |
| 6,015,064 | A | * | 1/2000 | Liu ............................. 220/524 |
| 6,019,225 | A | * | 2/2000 | Kalmakis et al. ........... 206/563 |
| 6,047,824 | A | * | 4/2000 | Winnard ..................... 206/350 |
| 6,098,802 | A | * | 8/2000 | Asa et al. .................... 206/443 |
| 6,164,449 | A | * | 12/2000 | Lahti .......................... 206/499 |
| 6,182,719 | B1 | | 2/2001 | Yahiro |
| 6,221,317 | B1 | * | 4/2001 | Carl ........................... 422/104 |
| 6,238,626 | B1 | * | 5/2001 | Higuchi et al. ............. 422/100 |
| 6,277,630 | B1 | * | 8/2001 | Brophy et al. ........... 435/288.4 |
| 6,286,678 | B1 | * | 9/2001 | Petrek ........................ 206/443 |
| 6,328,933 | B1 | * | 12/2001 | Labriola et al. ............ 422/104 |
| 6,358,470 | B1 | * | 3/2002 | Higuchi ........................ 422/63 |
| 6,405,870 | B1 | * | 6/2002 | Lahti et al. ................. 206/499 |
| 6,514,466 | B2 | * | 2/2003 | Labriola et al. ............ 422/104 |
| 6,534,015 | B1 | * | 3/2003 | Viot et al. .................. 422/102 |
| 6,575,209 | B2 | * | 6/2003 | Gora .......................... 141/238 |
| 6,759,012 | B2 | * | 7/2004 | Haslam et al. .............. 422/100 |
| 6,770,441 | B2 | * | 8/2004 | Dickinson et al. .............. 435/6 |
| 2002/0009398 | A1 | * | 1/2002 | Labriola et al. ............ 422/104 |
| 2002/0136821 | A1 | * | 9/2002 | Yamagata et al. ......... 427/2.11 |
| 2002/0153277 | A1 | * | 10/2002 | Bjork ......................... 206/701 |
| 2003/0064508 | A1 | * | 4/2003 | Kwasnoski et al. ...... 435/288.4 |
| 2003/0129089 | A1 | * | 7/2003 | Arnold et al. ................. 422/63 |
| 2003/0223910 | A1 | * | 12/2003 | Jackson et al. ............. 422/100 |
| 2004/0013576 | A1 | * | 1/2004 | Gfrorer et al. .............. 422/104 |
| 2004/0033168 | A1 | * | 2/2004 | Hughes et al. .............. 422/100 |
| 2004/0067170 | A1 | * | 4/2004 | Higuchi ...................... 422/100 |
| 2004/0171163 | A1 | * | 9/2004 | Lopez et al. ................. 436/63 |

OTHER PUBLICATIONS

//http://www.chem.mtu.edu/org/ctc/nsf_project.htm; "Determination and Modelling of Synergistic Effects of Carbon Based Conductive Fillers for Electrically and Thermally Conductive Resins".*
Steven Ashley, Electric Plastics, Mechanical Engineering, Apr. 1998.

* cited by examiner

CONDUCTIVE PLASTIC RACK FOR PIPETTE TIPS

This application claims the benefit of U.S. provisional application No. 60/275,761, filed Mar. 14, 2001.

BACKGROUND

The present invention relates generally to an electrically conductive plastic rack for pipette tips, and more particularly, it relates to an electrically conductive plastic rack for use with pipette tips following removal of the pipette tips from a plurality of pipettes.

Modem laboratory automation often involves conducting experiments using plates having multiple wells. These plates are known as "microplates". A typical microplate may contain three hundred and eighty four (384) wells or more. The microplate wells are used to hold specimens to be tested in a laboratory experiment. Pipettes are used to transfer liquids in and out of the microplate wells during the laboratory experiments. For example, the pipettes may transfer the initial specimens into the wells along with a number of different chemical reagents used during the laboratory experiment.

To prevent contamination of the pipettes when transferring liquid into and out of the microplate wells, a disposable polypropylene pipette tip is attached to the end of each pipette. The pipette tip carries all of the liquid to be transferred from one location to another, and prevents the actual pipette from contacting the liquid. After the transfer, the pipette tip is removed from the pipette and a new pipette tip is attached to the end of the pipette for subsequent transfers of different liquids. In this manner, precise concentrations, ingredient mixtures and amounts of liquids may be transferred using each pipette without the fear of contamination from a previous liquid transfer using the same pipette.

Multiple pipette devices are often used when conducting experiments using multiple well microplates. For example, a robotic device having three hundred eighty four (384) pipettes may be used when conducting experiments using a three hundred eighty four (384) well microplate. Such multiple pipette devices provide for the rapid removal or insertion of liquid into every microplate well. When using multiple pipette devices, tip racks are used to hold the pipette tips to be attached to the ends of the pipettes. The tip racks hold the tips in an organized fashion and allow the tips to be quickly inserted onto the pipettes or removed from the pipettes. Like the pipette tips, the tip racks are typically formed of polypropylene for ease of manufacture and cost savings. Because the tips and racks are both formed of relatively low cost polypropylene, it is customary in the industry to discard the tips and racks after a short period of time, or even after one use, for disposal and/or recycling.

With reference now to FIG. 1, the head 20 of a multiple pipette device 24 is shown. The head 20 holds three hundred eighty four pipettes 22 used to transfer liquid to and from a three hundred eighty four well microplate 50. Pipette tips 30 are shown inserted on each pipette 22 of the multiple pipette device 24. The pipette tips are positioned above a tip rack 40 used to hold the pipette tips 30 when they are removed from the pipettes 22 of the multiple pipette device 24.

Before the pipettes may be used to transfer liquid to and from the microplate wells, the tips 30 must be loaded onto the pipettes. A robotic arm (not shown) typically delivers a rack 40 full of tips 30 to the loading area 42. The head then positions itself directly above the rack 40 with each pipette in alignment with one of the tips 30. The head 20 then moves downward to bring the pipettes into contact with the tips 30. Each tip 30 is secured to a pipette with a friction-fit. Thus, the head must press (or be pulled) down with a substantial force to cause the tips to slide on to the ends of the pipettes. The sliding action of the polypropylene tips against the metal mandrels causes an electrostatic charge, i.e., triboelectricity, to develop on the exterior of the tips 30.

Once the tips are loaded onto the pipettes 22, the head 20 moves the pipettes and connected tips 30 to position the tips in the wells of the microplate 50. The pipettes then suck liquid from the wells and into the tips 30 for delivery to another location. After transferring liquid from one location to another (e.g., one microplate to another), the head returns to a position above the rack 40 so the head 20 is in position to return the used tips 30 to the rack. A shuck plate (not shown) then forces the tips from the pipettes, causing the tips 30 to fall into the tip rack 40 such that each tip is positioned in a tip seat on the tip rack. Of course, as the tips 30 are forced from the pipettes, they slide along the pipettes, once again causing an electrostatic charge to be generated and deposited upon the tips as a result of the rubbing action between the tips and the pipette. After the tips 30 are returned to the tip rack 40, the robotic arm may remove the rack full of tips for disposal or cleaning. Alternatively, the tips and rack may remain in place on the loading area for further use by the multiple pipette device.

Unfortunately, once the tips are returned to the rack, the triboelectric effect often creates a problem with the tips in the tip rack. In particular, when the polypropylene tips are returned to the polypropylene rack they each contain an electrostatic charge as a result of the rubbing action between the pipettes and tips during loading and unloading of the tips on the pipettes. The polypropylene tip rack does not conduct electricity. Thus, the static charges remain on the tips as they sit in the rack because there is no flow of the electric charge from the tips to the tip rack. The static charges on different tips and the rack itself cause some of the tips to repel away from each other and the rack. When the electrostatic charge is sufficient, this repelling action may cause one or more of the light-weight tips to become dislodged from the proper tip seats within the rack. In the worst situations, one or more tips may jump completely out of the tip rack as a result of the electrostatic forces between tips. When a tip becomes dislodged from a tip seat or jumps completely out of the tip rack, significant problems arise because loose tips may be lost and not properly discarded and removed from the testing area. Also, if in a subsequent step of a laboratory process the head is scheduled to return to the tip rack and once again join the pipettes to the used set of tips, an improperly seated tip on the tip rack may be crushed by the force of the head as the head moves the pipettes into position to pick up the tips. This may result in operational failure of the multiple pipette device and/or faulty experiment results.

For the foregoing reasons there is a need for a multiple pipette system that will prevent tips from becoming displaced in the tip rack as a result of the triboelectric effect during loading and unloading of the tips. In addition, there is a need for a tip rack for use with a multiple pipette system that will prevent electrically charged tips from becoming displaced within the rack.

SUMMARY

The present invention is directed to an apparatus that satisfies the need for a tip rack for use with a multiple pipette system that prevents electrically charged pipette tips from becoming displaced within the tip rack. The apparatus is a tip rack comprising a face having a plurality of seats formed thereon for holding pipette tips and at least one sidewall depending from the face. The face and the at least one sidewall of the tip rack are integrally formed as a one-piece conductive outer shell. The tip rack further comprises a support insert connected to the conductive outer shell such that the support insert is covered by the conductive outer shell. The support insert includes a plurality of support walls that form chambers dimensioned to receive the pipette tips.

The face and the at least one sidewall are comprised of an electrically conductive plastic material whereby static electricity deposited on the pipette tips is discharged through the tip rack when the pipette tips contact the tip rack. A number of different electrically conductive plastic materials may be used to form the tip rack. For example, the electrically conductive plastic material may include polypropylene impregnated with carbon, metal flakes, metal powder or metal strands. In one preferred embodiment of the invention, the tip rack comprises about 15% or more carbon, by weight, and preferably, about 21% carbon, by weight.

When pipette tips having an electric charge deposited thereon are contacted with the tip rack, the electric charge deposited on the pipette tips is conducted through the electrically conductive tip rack and either delivered to ground or dissipated on the tip rack. Thus, when the pipette tips are seated in the tip rack, the pipette tips will not be displaced in the tip rack because any significant electrostatic charges on the pipette tips are conducted away from the pipette tips and through the tip rack. These and other features, aspects, and advantages of the present invention will become better understood with reference to the following description and the appended claims.

DESCRIPTION

Figure 1:
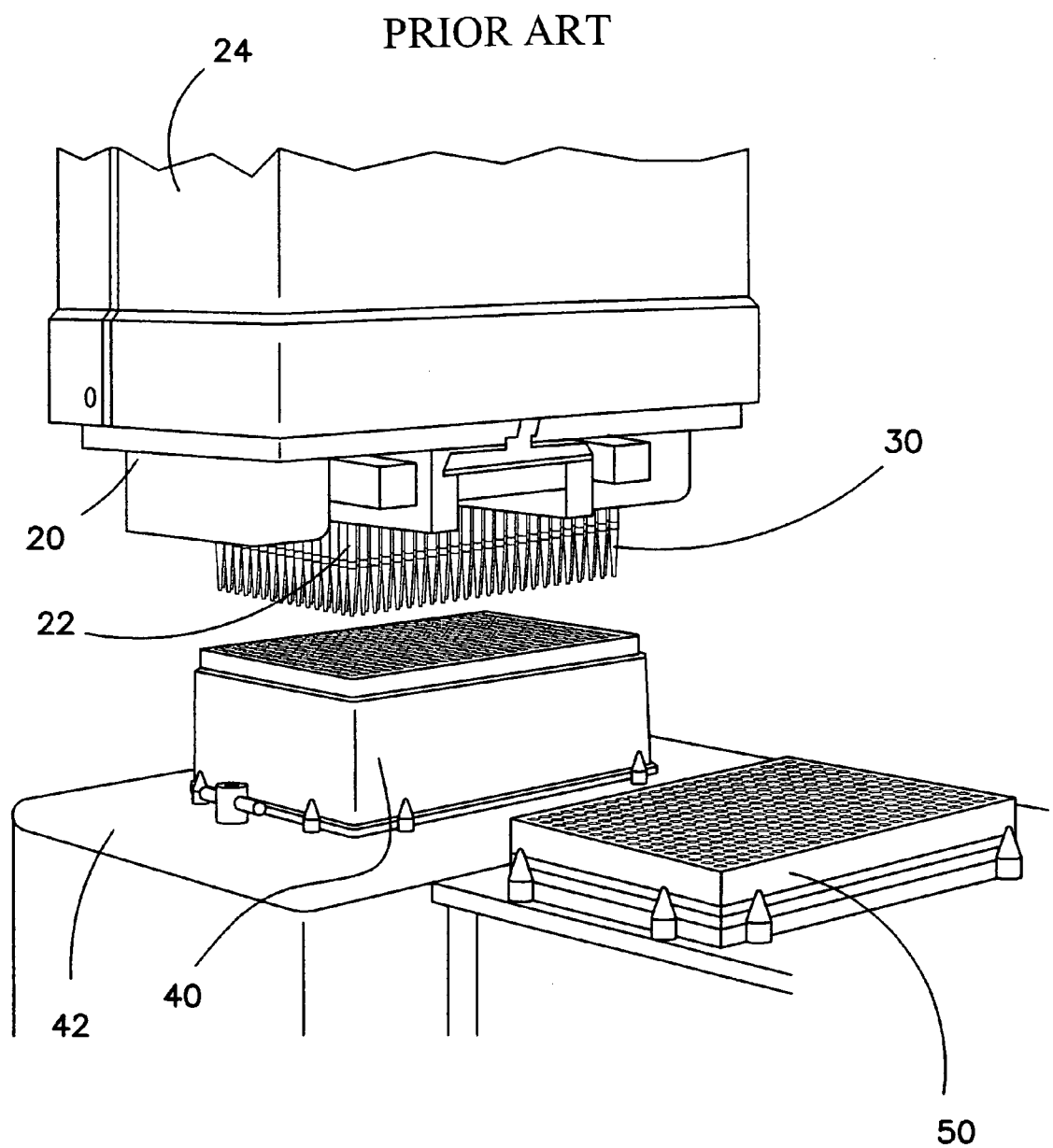
FIG. 1 shows a perspective view of a multiple pipette device holding tips positioned over a tip rack.
Figure 2:
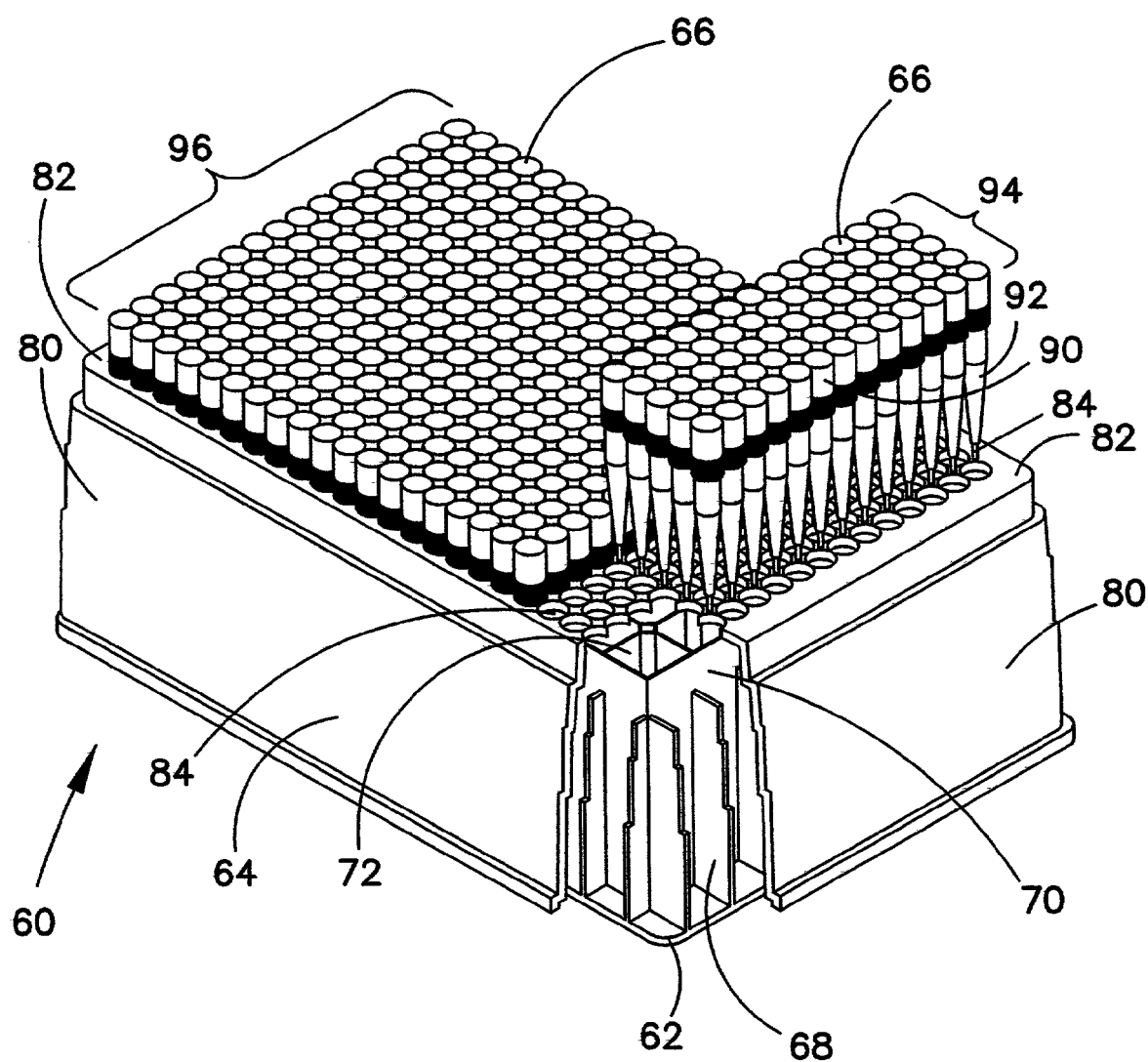
FIG. 2 shows a perspective view and cutaway portion of the conductive plastic rack for pipette tips.

With reference to FIG. 2, a conductive plastic tip rack 60 for pipette tips is shown. The conductive plastic rack includes a conductive outer shell 64 formed around a support insert 62. The support insert 62 is manufactured separate from the conductive outer shell 64, and the two pieces are designed to easily fit together to form the complete rack 60. For example, the support insert 62 and conductive outer shell 64 may snap-fit, or be joined using other connection means (e.g., screws, adhesives, etc.).

The conductive outer shell 64 is designed to receive the pipette tips 66. The conductive outer shell includes sidewalls 80 depending from the sides of a face 82, and a number of tip seats 84 formed upon the face 82. The tip seats are holes in the face 82 and are arranged in a rectangular fashion to form a matrix of tip seats. In the preferred embodiment of the invention, the face 82 and the sidewalls are integrally formed as a single piece to make up the conductive outer shell 64.

The conductive outer shell 64 is formed of any number of different plastics capable of conducting electricity or dissipating electricity. In one embodiment of the invention, the conductive outer shell is formed mostly of polypropylene and is filled with other material to make the outer shell conductive. For example, the polypropylene may be impregnated with about 15% or more carbon, by weight, to make the plastic conductive. Polypropylene impregnated with about 21% carbon, by weight, is one preferred conductive plastic, such as that manufactured by the RTP Company of Winona, Minn. However, any number of different materials, may be used for the conductive outer shell. For example, in addition to the use of carbon, the plastic may also be made conductive by including metal strands, metal flakes, metal powder in the plastic. Furthermore, instead of impregnating materials into the plastic before the rack is molded to its desired shape, the conductive plastic rack may be formed by coating on the exterior of the rack with conductive plastic material or metallic material.

The conductive plastic rack is capable of sufficiently conducting or dissipating electricity such that the electricity deposited on a tip placed within the tip rack will flow out of the tip and through the tip rack, thereby prevent the tip from repelling other tips within the rack with any forces significant to disturb the seated position of the other tips within the tip rack. To this end, the tip rack may be grounded to allow static electricity flowing through the tip rack to be grounded. However, if the tip rack is not grounded, the surface area of the rack is sufficiently large to dissipate significant concentrations of static electricity throughout the rack, and avoid any problems wherein pipette tips are dislodged from their seats. Accordingly, the term "conductive plastic" as used herein is intended to cover both electrically conductive plastics and static dissipative plastics.

The support insert 62 serves as the skeleton for the plastic rack, providing structural support to make the rack 60 strong and sturdy. The support insert 62 is preferably made of polypropylene and may or may not include other material such as graphite to make the insert conductive. Although the support insert 62 is completely covered by the conductive outer shell 64, FIG. 2 shows a cutaway portion of the conductive outer shell that reveals the support insert 62. The insert 62 provides a number of support walls 70 that form chambers 72 for receiving pipette tips 66 when they are inserted into the rack. The support walls 70 provide a lightweight honeycomb structure that allows the face of the conductive outer shell to support a large amount of force. It is important that the face supports a large amount of force because of the substantial force exerted upon the face when the pipettes are attached to the pipette tips sitting in the rack. In addition, the support insert 62 includes a number of buttresses 68 around the outer support walls. These buttresses 68 fit against the sidewalls 80 of the conductive outer shell 64 when the conductive outer shell is joined to the insert 62, thereby providing additional structural support for the conductive outer shell. The two-part rack comprised of the conductive outer shell 64 and the support insert 62 may be manufactured for less cost than a one-piece rack because the more expensive conductive plastic material is only required to form the conductive outer shell 64, and the support insert 62 may be made of less expensive non-conductive plastic.

Each pipette tip 66 is made of polypropylene and includes a collar portion 90 and a conical body 92. The collar portion 90 includes and interior diameter, and this interior diameter of the collar portion is designed to securely fit around the end of a pipette held by the multiple pipette device and thereby attache the pipette tip to the pipette. The conical body 92 is the portion of the tip that receives and dispenses liquid to be transferred from one location to another. FIG. 2 shows a first portion 94 of the pipette tips removed from their seats 84 and a second portion 96 of the pipette tips positioned within their seats on the tip rack 60. As shown by the first portion 94 of the pipette tips, each pipette tip is placed in the rack by inserting the conical body of the pipette tip into one of the seats 84. As shown by the second portion 96 of pipette tips, when a pipette tip is properly positioned in a seat 84, the collar portion 90 of the pipette tip rests against the face 82 of the conductive outer shell 64 and the conical body 92 is received within one of the chambers 72 of the support insert. Thus, the diameter of each pipette seat 84 is large enough to pass the conical body 92 of a pipette tip, but small enough to prevent passage of the collar portion 90.

In operation, a robot transfers the rack 60 with seated polypropylene tips 66 to a loading area where a multiple pipette device will pick up the tips positioned within the rack. The head of the multiple pipette device comes into position over the rack 60 and the pipettes are inserted into the collars 90 of the pipette tips. The rubbing of the pipette tips with the collars creates a static electric charge on the tips. After the pipettes and their associated tips have been used to transfer liquids from one location to another, the tips are removed from the pipettes by the shuck plate (not shown). Once again, when the tips are removed from the pipettes, the tip collars 90 rub against the pipettes and electrostatic charges are generated and deposited upon the tips. However, when the tips fall into the seats of the tip rack and come into contact with the conductive outer shell of the rack, the electrostatic charge is conducted from the tips and through the rack to ground or dissipated within the rack. Thus, when the tips are placed in the rack, the tips do not repel against each other or the rack and are held securely in place within the rack by gravity. In this manner, the conductive plastic rack for pipette tips prevents random failures resulting from electrostatic charges on the tips, and therefore makes operation of the multiple pipetting device more reliable.

Various tests were performed using the conductive plastic tip rack in a laboratory setting. In one test, the conductive outer shell was formed of polypropylene material impregnated with carbon such that the carbon comprised about 21% of the total weight of the polypropylene material. With this 21% carbon, by weight, polypropylene material, the tip rack reliably removed the problem of tips repelling within the tip rack at 17% relative humidity. It was found that in very low humidity testing environments of less than 10% relative humidity, additional humidity is sometimes required to prevent any significant repelling of the tips within the rack using the conductive outer shell formed of polypropylene material having about 21% carbon, by weight. However, other conductive or dissipative outer shells formed of other plastics may perform even more reliably in low humidity conditions.

Although the present invention has been described in considerable detail with reference to certain preferred versions thereof, other versions are possible. For example, the rack may be a single molded conductive piece and need not be comprised of an insert with a conductive outer shell. As another example, the tips themselves may also be manufactured of a conductive plastic material. Of course, many other versions of the invention are possible. Therefore, the spirit and scope of the invention should not be limited to the description of the preferred versions contained herein.

The invention claimed is:

1. A method of discharging static electricity from a plurality of pipette tips held by a plurality of pipettes, the method comprising:
   a. providing a tip rack comprised of an electrically conductive plastic material, the tip rack including a face with a plurality of seats formed thereon for holding pipette tips;
   b. removing the plurality of pipette tips from the plurality of pipettes; and
   c. seating the plurality of pipette tips in the plurality of seats such that the static electricity deposited on the pipette tips is discharged through the tip rack when the pipette tips are contacted with the tip rack.

2. The method of claim 1 wherein the static electricity is discharged through the tip rack by conducting the static electricity to ground when the pipette tips are contacted with the tip rack.

3. The method of claim 1 wherein the static electricity is discharged through the tip rack by dissipating the static electricity on the surface of the tip rack when the pipette tips are contacted with the tip rack.

4. The method of claim 1 wherein the tip rack includes a one-piece conductive outer shell comprising the face, and the tip rack further includes a support insert connected to the conductive outer shell such that the support insert is covered by the conductive outer shell.

5. The method of claim 1 wherein the step of removing the plurality of pipette tips from the plurality of pipettes results in the generation of additional static electricity on the pipette tips that is discharged through the tip rack when the pipette tips are contacted with the tip rack.

6. The method of claim 1 wherein static electricity discharged through the tip rack is directed to ground.

7. The method of claim 1 wherein static electricity discharged through the tip rack is dissipated on the electrically conductive plastic material.

* * * * *